(12) United States Patent
Hirano

(10) Patent No.: US 7,242,471 B2
(45) Date of Patent: Jul. 10, 2007

(54) GLOW DISCHARGE OPTICAL EMISSION SPECTROMETER AND GLOW DISCHARGE OPTICAL EMISSION SPECTROMETRY

(75) Inventor: Akihiro Hirano, Kyoto (JP)

(73) Assignee: Horiba, Ltd., Kyoto (JP)

( * ) Notice: Subject to any disclaimer, the term of this patent is extended or adjusted under 35 U.S.C. 154(b) by 149 days.

(21) Appl. No.: 11/220,033

(22) Filed: Sep. 6, 2005

(65) Prior Publication Data

US 2006/0055924 A1 Mar. 16, 2006

(30) Foreign Application Priority Data

Sep. 13, 2004 (JP) ............... 2004-266048

(51) Int. Cl.
*G01J 3/30* (2006.01)
*G01N 21/66* (2006.01)
(52) U.S. Cl. ..................... 356/311
(58) Field of Classification Search ......... 356/311
See application file for complete search history.

(56) References Cited

FOREIGN PATENT DOCUMENTS

| JP | 11-326217 | * 11/1999 |
| JP | 2001-004548 | 1/2001 |

OTHER PUBLICATIONS

Wagatsuma, K, "Improvement of the Information Depth in In-Depth Analysis By Radio-Analysis By Radio-Frequency-Powered Glow Discharge Optical Emission Spectrometry", ISIJ INTERNATIONAL, vol. 42, 2002, pp. S87-S92.

Wagatsuma, K, Application of Pulsed Voltage to D.C. Glow Discharge Plasma for Controlling the Sputtering Rate in Glow Discharge Optical Emission Spectrometry, ISIJ INTERNATIONAL, vol. 44, 2004, pp. 108-114.

Wagatsuma, K, Application of DC Voltage Modulation Technique to the Determination of Phosphorous and Sulfur in Steel Samples in Glow Discharge Optical Emission Spectrometry, ISIJ INTERNATIONAL, vol. 40, pp. 783-788.

Wagatsuma et al., Enhancement Factor in the Emission Intensities Excited by Radiofrequency-powered Glow Discharge Plasma Associated with Bias-current Introduction, ISIJ INTERNATIONAL, vol. 41, 2001, pp. 1488-1493.

* cited by examiner

*Primary Examiner*—F. L. Evans

(57) ABSTRACT

The invention provides a glow discharge optical emission spectrometer for intermittently applying a high frequency voltage to a sample and obtaining a measured value from a spectroscope in synchronization with a timing of a unit of application during intermittent application. The obtaining of measured values in which is introduced noise at a non-application time during intermittent application is prevented, and by applying a high voltage value to the sample with a minimized adverse effect on a voltage application to the sample, high-level measured values are obtained. By obtaining a measured value a plural number of times during a unit of application, a large number of measured values are obtained in a short period of time, resulting in a reduction in measurement time.

10 Claims, 12 Drawing Sheets

FIG. 10

| MODE SELECTION | FREQUENCY SETTING | OCCUPIED RATIO SETTING |
|---|---|---|
| INTERMITTENT APPLICATION MODE | 1 Hz | 0.125 |
| CONTINUOUS APPLICATION MODE | 2 | 0.0625 |
| | 3 | 0.125 |
| | 4 | 0.1875 |
| | 5 | 0.25 |
| SETTING FOR NUMBER OF MEASUREMENTS | 6 | 0.3125 |
| 1 | ⋮ | ⋮ |
| 2 | | 0.875 |
| 3 | 3000 | 0.9375 |
| ⋮ | | |
| 100 | | |

~20

GLOW DISCHARGE OPTICAL EMISSION SPECTROMETER AND GLOW DISCHARGE OPTICAL EMISSION SPECTROMETRY

CROSS-REFERENCE TO RELATED APPLICATIONS

This Nonprovisional application claims priority under 35 U.S.C. §119(a) on Patent Application No. 2004-266048 filed in Japan on Sep. 13, 2004, the entire contents of which are hereby incorporated by reference.

BACKGROUND OF THE INVENTION

The present invention relates to a glow discharge optical emission spectrometer with which high-level and highly-accurate measured values can be obtained in a short period of time by performing an intermittent application in which an application of a high frequency voltage and a non-application are intermittently switched, and obtaining a measured value at a timing in synchronization with an application timing, and a glow discharge optical emission spectrometry.

Conventionally, there exists a glow discharge optical emission spectrometer which causes light emission from a glow discharge by applying a high frequency voltage to a sample, splits the light emission by wavelength with a spectroscope and measures the intensities of the split lights, and then feeds the measured values into an analytical device such as a computer, thereby analyzing the composition of the sample.

In a conventional glow discharge optical emission spectrometer, a sample which is the object to be analyzed is disposed at a glow discharge tube, an inert gas is supplied onto the sample surface, and then a high frequency voltage (alternating voltage) on the order of 13 MHz is applied to the sample from a power supply section to generate a glow discharge, and the spectra of light emission caused by sputtering associated with the glow discharge are measured, whereby the analysis of the sample is performed (see Japanese Patent Application Laid-Open No. 2001-4548).

BRIEF SUMMARY OF THE INVENTION

The conventional glow discharge optical emission spectrometer presents a problem in that it is difficult to obtain good measurement results in the case of performing a quantitative analysis (bulk analysis) on a metallic material, i.e., in the case of performing a measurement to determine what elements and what concentrations of those elements are contained in various metallic materials such as steel and aluminum.

Specifically, a metallic material, which is the object to be measured and is disposed at the glow discharge tube, faces an electrode with a certain distance therebetween and sputtering is caused between the sample and the electrode upon start of a voltage application. In measuring a metallic material, generally, a continuous voltage application is performed for a long period of time, and therefore, sputtering also continues for a long period of time. Furthermore, since sputtering causes attrition of the surface of the metallic material, as the application time elapses, the distance from the surface of the metallic material to the electrode increases due to the influence of sputtering.

As a result, the conditions under which sputtering occurs are changed, and accordingly, light emission becomes unstable, and by the increase of the distance between the metallic material and the electrode the measured intensity of the metallic material gradually reduces (see FIG. 1). Consequently, it becomes difficult to obtain stable measurement results, and an inexperienced measurer or the like may be mislead to believe that the measured value is changed.

Furthermore, in a glow discharge optical emission spectrometer, the higher the value of a voltage applied to the sample, the higher the intensity of light emission and thus good, high-level measured values can be obtained. However, by increasing the voltage value, sputtering caused between the metallic material and the electrode increases, and accordingly, attrition of the metallic material caused by sputtering progresses in a short period of time, which in turn accelerates the time when the measurement becomes unstable. Accordingly, in the conventional glow discharge optical emission spectrometer, the measurement needs to be performed at low voltage values so as to diminish the degree of attrition caused by sputtering, and thus, there is a problem in that good measurement results cannot be obtained in a short period of time.

In view of the foregoing problems, an object of the present invention is to provide a glow discharge optical emission spectrometer with which good measurement results with little noise component can be obtained in a short period of time by intermittently applying a voltage to prevent, even at high voltage values, attrition of the sample from progressing in a short period of time, and obtaining a measured value in synchronization with an intermittent application, and a glow discharge optical emission spectrometry.

Another object of the present invention is to provide a glow discharge optical emission spectrometer with which measurement results which are good and easily understandable for a measurer can be obtained for various types of samples.

In a glow discharge optical emission spectrometer according to a first aspect, for measuring, with a spectroscope, an intensity of light emission from a glow discharge generated by application of an alternating voltage to a material to be analyzed, the glow discharge optical emission spectrometer comprises: intermittent application means for intermittently applying an alternating voltage to the material to be analyzed; and measured value obtaining means for obtaining a value measured by the spectroscope, in synchronization with an intermittent application which is performed by the intermittent application means.

By intermittently applying an alternating voltage to a material to be analyzed, sputtering caused by voltage application becomes sporadic and thus the degree of attrition of the material to be analyzed is diminished; accordingly, a higher voltage value than that of conventional cases can be applied without causing problems, and thus, high-level measured values can be obtained. In addition, since values which are continuously measured with the spectroscope are obtained in synchronization with an intermittent application and a measured value is not obtained at a non-application time during intermittent application, various noise components generated during a non-application time can be removed from the measurement results, and thus, highly-accurate measurement results can be obtained. Note that the obtaining of a measured value in synchronization with an intermittent application can be realized by either a hardware configuration or a software process.

In a glow discharge optical emission spectrometer according to a second aspect, the measured value obtaining means obtains a measured value from the spectroscope a plurality of times per application during one cycle of intermittent application. Since a measured value is obtained a plurality of times per application time which constitutes one cycle during intermittent application, even when an intermittent application is performed, a large number of measurement results can be obtained in a short period of time, and the measurement can be completed in a short period of time before an adverse effect on the material to be analyzed caused by sputtering becomes noticeable. Note that one cycle of intermittent application means a cycle which consists of one application and one non-application during intermittent application.

A glow discharge optical emission spectrometer according to a third aspect comprises number-of-times reception means for receiving a number of times to obtain a measured value per application during one cycle of intermittent application, and the measured value obtaining means obtains from the spectroscope a measured value the number of times received by the number-of-times reception means. The number of times to obtain a measured value per application time during one cycle can be received, and such number of times can be changed. Since a measured value is obtained in accordance with the number of times thus received, the measurement can be performed such that the number of times to obtain a measured value is flexibly changed according to the frequency of a voltage to be intermittently applied, an application time for one cycle, the type of a material to be analyzed, and the like.

A glow discharge optical emission spectrometer according to a fourth aspect comprises means for creating continuous-graph data in which the measured values obtained by the measured value obtaining means are associated with application times during intermittent application. Since continuous-graph data is created based on measured values which are separated by time, such that the measured values are associated with times at which a voltage application is performed, a measurer can check a graph in which the measured values are connected with respect to the time axis in which individual application times are converged, and accordingly, even when an intermittent voltage application is performed, the measurer can easily judge measurement results.

A glow discharge optical emission spectrometer according to a fifth aspect comprises means for calculating an average measured value of the measured values obtained by the measured value obtaining means, for an application time or a number of measurements. Since the average measured value of measured values is calculated based on an application time or the number of measurements, it becomes easier for the measurer to understand measurement results, and the analysis of a material to be analyzed can be easily performed.

A glow discharge optical emission spectrometer according to a sixth aspect comprises timing instruction means for instructing the intermittent application means about an application timing for an application of one cycle of intermittent application, and the measured value obtaining means obtains a measured value at the timing instructed by the timing instruction means. By obtaining a measured value at a timing at which an instruction to apply a voltage is given to each cycle, a measured value can be obtained easily and surely in synchronization with an intermittent voltage application. Note that for the timing instruction means for instructing about an application timing it is preferable to employ a hardware configuration; for example, a device can be employed which outputs a signal for controlling an application timing for the intermittent application means which intermittently applies an alternating voltage.

A glow discharge optical emission spectrometer according to a seventh aspect comprises application detection means for detecting an application of an alternating voltage to the material to be analyzed, and the measured value obtaining means obtains a measured value at a timing at which the application detection means detects the application of an alternating voltage. By detecting an application of an alternating voltage to the material to be analyzed and obtaining a measured value at a timing of detection, a measured value can be surely obtained at a timing close to a timing at which light emission occurs, which contributes to improvement of the accuracy of the measurement level. Note that for the application detection means for detecting an application of an alternating voltage, it is preferable to employ a hardware configuration in view of surely obtaining a measured value.

A glow discharge optical emission spectrometer according to an eighth aspect comprises time reception means for receiving a proportion of an application time in one cycle of intermittent application, and the intermittent application means performs an intermittent application based on the proportion of an application time received by the time reception means. Since the proportion of an application time in one cycle can be received and an intermittent voltage application is performed in accordance with the received proportion of an application time to one cycle, it is possible to provide the optimum voltage application mode in accordance with the characteristics of the substance of the material of various materials to be analyzed. Namely, since the degree of attrition caused by sputtering varies with the type of a material to be analyzed, by adjusting the proportion of an application time in accordance with the characteristics of the material to be analyzed, a good measurement and a good analysis can be performed.

A glow discharge optical emission spectrometer according to a ninth aspect comprises number-of-times reception means for receiving a number of applications per unit time for intermittent application, and the intermittent application means performs an intermittent application based on the number of applications received by the number-of-times reception means. Since the number of applications per unit time, i.e., the frequency for intermittent application, can be received and an intermittent application is performed in accordance with the received contents, a voltage application mode in accordance with the characteristics of the material to be analyzed is ensured, which contributes to the completion of the measurement in a short period of time. Furthermore, since in the material to be analyzed there is present a frequency suitable for analysis, at which the elements composing the substance of the material can be easily detected, by appropriately adjusting the frequency, the conditions under which the analysis is easily performed can be set.

In a glow discharge optical emission spectrometry according to a tenth aspect using a glow discharge optical emission spectrometer having a voltage application section, a spectroscope, and an analysis control section, in which a glow discharge is generated by application of an alternating voltage to a material to be analyzed by means of the voltage application section, an intensity of light emission from the glow discharge is measured with the spectroscope, and a value measured by the spectroscope is obtained by the analysis control section, the glow discharge optical emission spectrometry comprises the steps of: intermittently applying an alternating voltage to the material to be analyzed by the voltage application section; and obtaining a value measured by the spectroscope by the analysis control section in synchronization with an intermittent application to the material to be analyzed. By intermittently applying an alternating voltage to the material to be analyzed, an application at a higher voltage value than that of conventional cases can be performed. By obtaining a measured value in accordance with an intermittent application, noise components can be removed. Consequently, high-level and highly-accurate measurement results can be obtained.

The above and further objects and features of the invention will more fully be apparent from the following detailed description with accompanying drawings.

BRIEF DESCRIPTION OF THE SEVERAL VIEWS OF THE DRAWINGS

FIG. 10 is a schematic diagram showing a menu screen;

DETAILED DESCRIPTION OF THE INVENTION

The present invention will be described in detail below with reference to the drawings showing an embodiment thereof.

Figure 1:
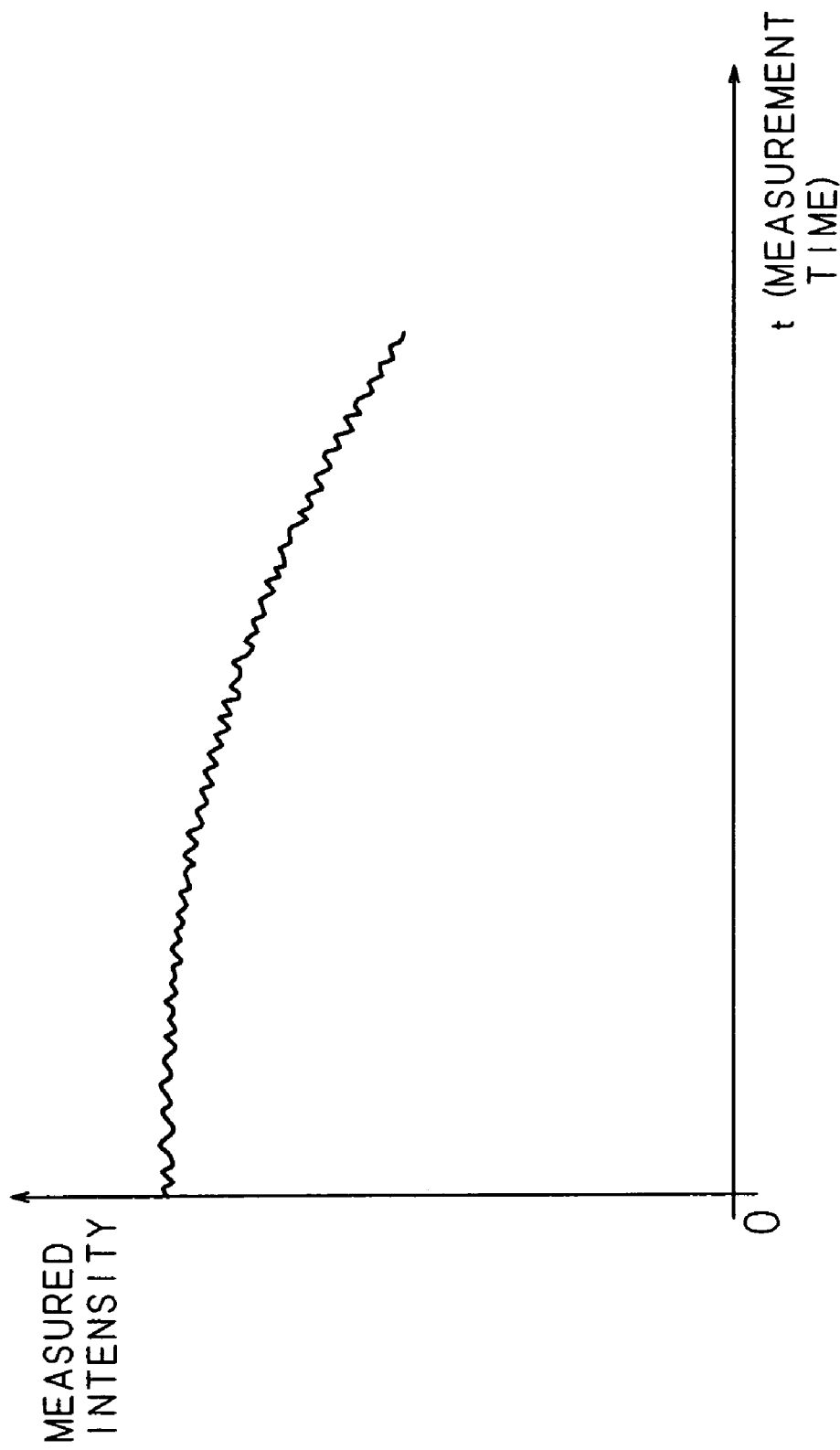
FIG. 1 is a graph showing conventional measurement results.
Figure 2:
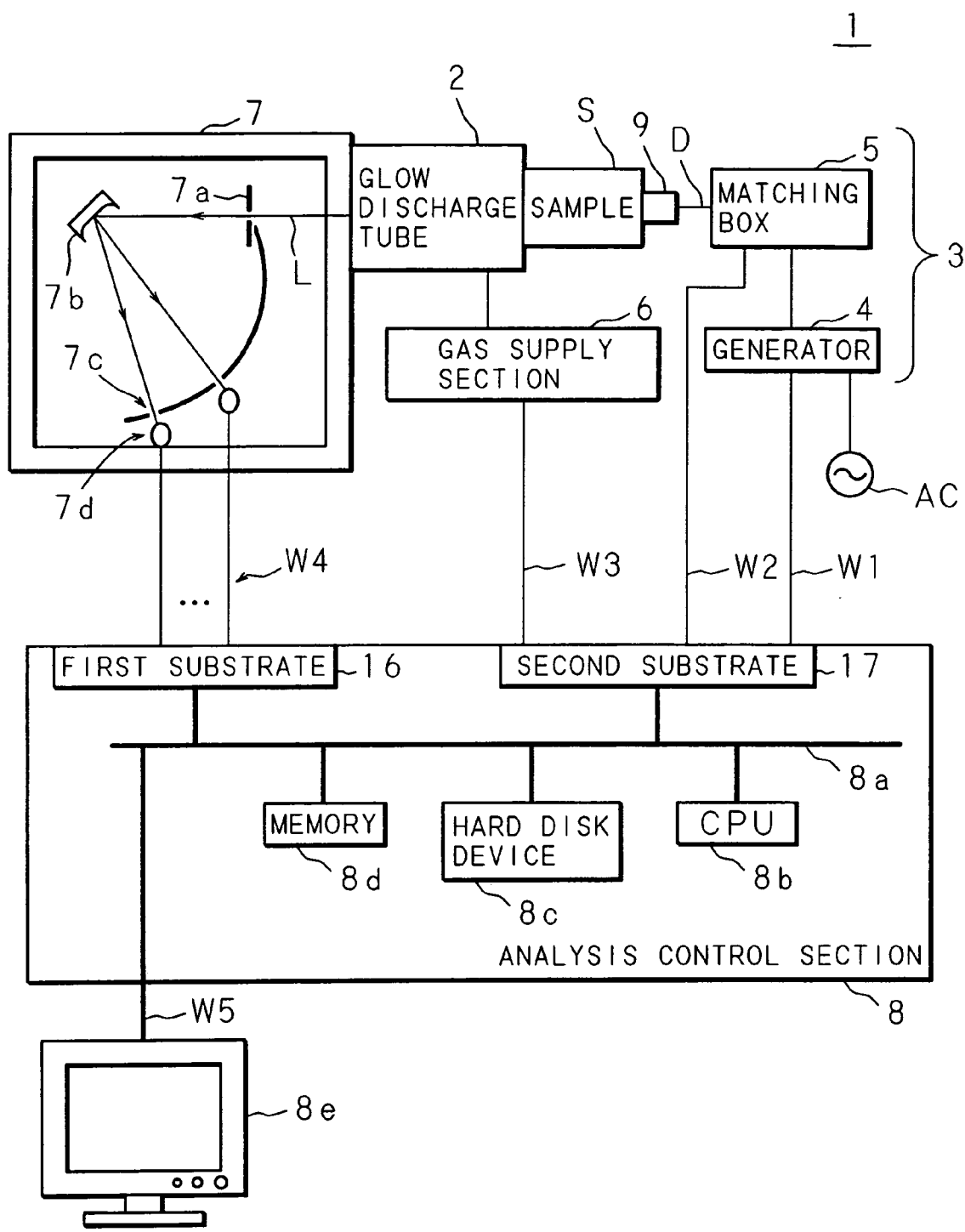
FIG. 2 is a schematic diagram showing the overall glow discharge optical emission spectrometer according to an embodiment of the present invention.

FIG. 2 is a schematic diagram showing the overall configuration of a glow discharge optical emission spectrometer 1 according to an embodiment of the present invention. The glow discharge optical emission spectrometer 1 includes a glow discharge tube 2 for causing a glow discharge to be generated on a sample S which is the material to be analyzed; a power supply section 3 for applying a high frequency voltage to the glow discharge tube 2; a gas supply section 6 for supplying to the glow discharge tube 2 a gas necessary for the measurement; a spectroscope 7 for splitting light L generated from the glow discharge tube 2 into lights and measuring the intensity of each split light; and an analysis control section 8 for obtaining the measured values and performing an analysis on the composition of the samples. The power supply section 3 is connected to an alternating-current power supply AC (220 V in the present embodiment), and has a generator 4 for generating a high frequency voltage and a matching box 5.

Figure 3:
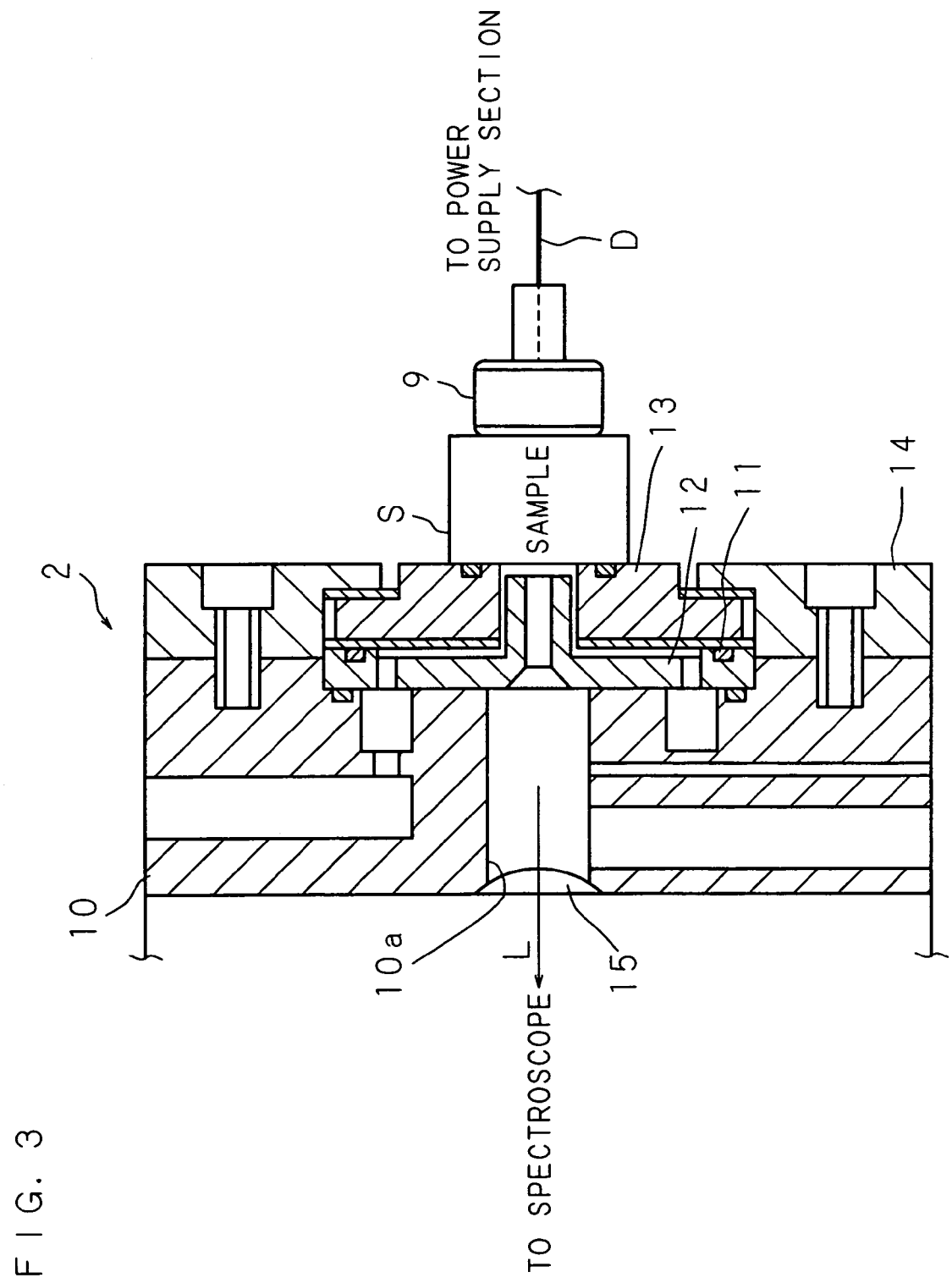
FIG. 3 is a schematic cross-sectional view of a glow discharge tube.

As shown in FIG. 3, the glow discharge tube 2 is configured such that an anode 12 and ceramics 13 with an insulating material 11 provided therebetween are mounted to a lamp body 10 having a through-hole 10a provided therein, by means of a pressing block 14. A condensing lens 15 is disposed at an end of the through-hole 10a which is on the side of the spectroscope 7 and into which an inert gas is introduced from the gas supply section 6. Further, the sample S is mounted onto the ceramics 13 with a sample pressing member 9 pressing the sample S. The sample pressing member 9 also serves as a voltage application electrode. The sample pressing member 9 is connected, through a power supply line D, to the power supply section 3 which corresponds to a voltage application section, and applies a high frequency voltage from the power supply section 3 to the sample S.

Figure 4:
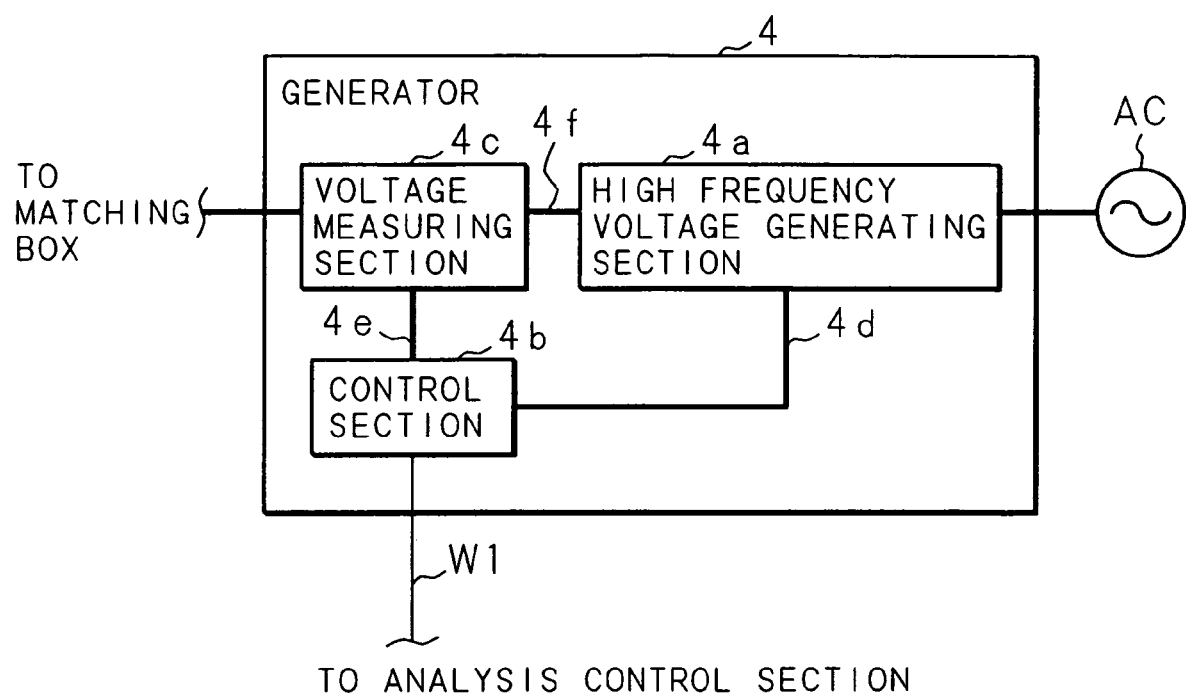
FIG. 4 is a block diagram showing an internal configuration of a generator.

As shown in FIG. 4, the generator 4 of the power supply section 3 incorporates a high frequency voltage generating section 4a, a control section 4b, and a voltage measuring section 4c. The high frequency voltage generating section 4a is connected to the alternating-current power supply AC, and generates a high frequency voltage (alternating voltage) in which the voltage changes from positive to negative or vice versa in the form of a high frequency. In addition, the high frequency voltage generating section 4a is connected to the control section 4b through a first internal connecting line 4d, and adjusts the output mode and voltage value of a high frequency voltage by control of the control section 4b. The high frequency voltage generating section 4a of the present embodiment generates a high frequency voltage of 13.56 MHz.

The control section 4b of the generator 4 is composed of an IC (integrated circuit). The control section 4b controls to switch the output mode of a high frequency voltage, which is generated by the high frequency voltage generating section 4a, between two types based on a signal instructing about the voltage application mode, which is outputted from the analysis control section 8 through a first connecting cord W1.

Figure 5:
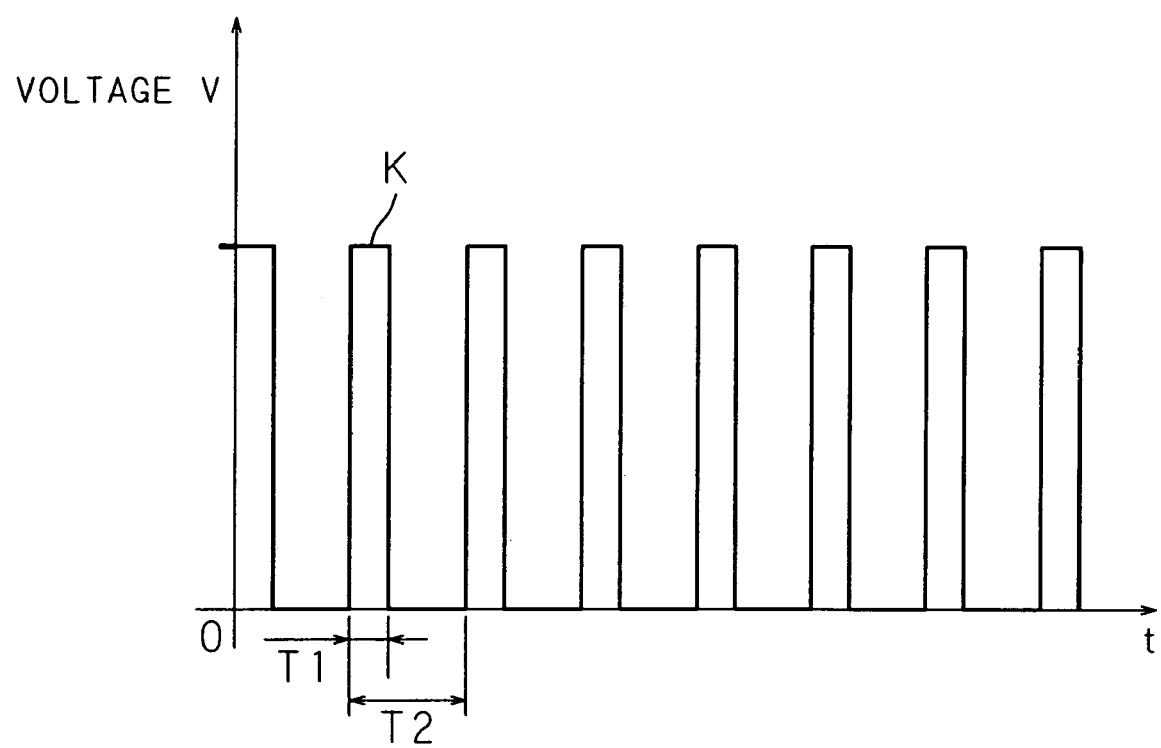
FIG. 5 is a graph showing a state of an intermittent application by the generator in an intermittent application mode.

The first output mode is, as shown in FIG. 5, a pattern (hereinafter referred to as the "intermittent application mode") in which a high frequency voltage is intermittently applied by alternately and intermittently switching between an application of a voltage and a non-application by means of the IC. In the intermittent application mode, the generator 4 functions as an intermittent application means, and a high frequency voltage generated by the high frequency voltage generating section 4a is applied to the sample S only during a unit of application time T1 corresponding to one unit of application K which projects in the form of a rod, as shown in FIG. 5. In the intermittent application mode, one cycle consists of one unit of application K and one non-application, and the time required for one cycle is T2 (see FIG. 5). The second output mode is a pattern (hereinafter referred to as the "continuous application mode") in which a voltage application is continuously performed from the start to the end.

In the case of the intermittent application mode, the control section 4b of the generator 4 controls to adjust the number of applications (which corresponds to an application frequency) per unit time (one second) for intermittent application, based on a signal outputted from the analysis control section 8. The control section 4b of the present embodiment is capable of adjusting the application frequency in a range from 1 Hz to 3000 Hz. Note that when the application frequency is changed, time T2 of one cycle in the graph shown in FIG. 5 also changes.

Furthermore, in the case of the intermittent application mode, the control section 4b controls to change the unit of application time T1 based on a signal outputted from the analysis control section 8. Specifically, the control section 4b receives a signal indicating the proportion (T1/T2; which is referred to as the "occupied ratio to voltage application") occupied by a unit of application time T1, which corresponds to one voltage application, in time T2 corresponding to one cycle during intermittent application, shown in FIG. 5, from the analysis control section 8 through the first connecting cord W1, and then makes an adjustment based on the signal.

Moreover, the control section 4b performs a process of making an adjustment according to the change in the impedance value of the sample S which is caused by sputtering. The specific contents of the process is as follows. The control section 4b calculates the difference between an output value Pf and a reflection value Pr which are transmitted from the voltage measuring section 4c included in the generator 4, and then controls, based on the calculated difference, to change the voltage value (output value Pf) of the traveling wave of a high frequency voltage which is generated by the high frequency voltage generating section 4a and applied to the sample S. At this time, the control section 4b adjusts the output value Pf of the high frequency voltage in a software manner using the IC incorporated in the control section 4b, such that the calculated difference (Pf−Pr) becomes equal to a reference voltage value transmitted from the analysis control section 8.

Note that an adjustment made by the control section 4b according to the change in the impedance value of the sample S is for the case of the intermittent application mode. In the continuous application mode, an adjustment is made by the matching box 5 of the power supply section 3, as will be described later.

The voltage measuring section 4c of the generator 4 is connected to the control section 4b and the high frequency voltage generating section 4a through second and third internal connecting lines 4e and 4f, respectively. The voltage measuring section 4c detects each of an output value Pf of the traveling wave of a high frequency voltage which is generated by the high frequency voltage generating section 4a and outputted to the sample S, and a reflection value Pr which is the voltage value of a reflected wave reflected and returned from the sample S. In addition, in order that the control section 4b can make the above-described adjustment according to the change in the impedance value of the sample S, the voltage measuring section 4c transmits the detected output value Pf and reflection value Pr to the control section 4b.

Figure 6:
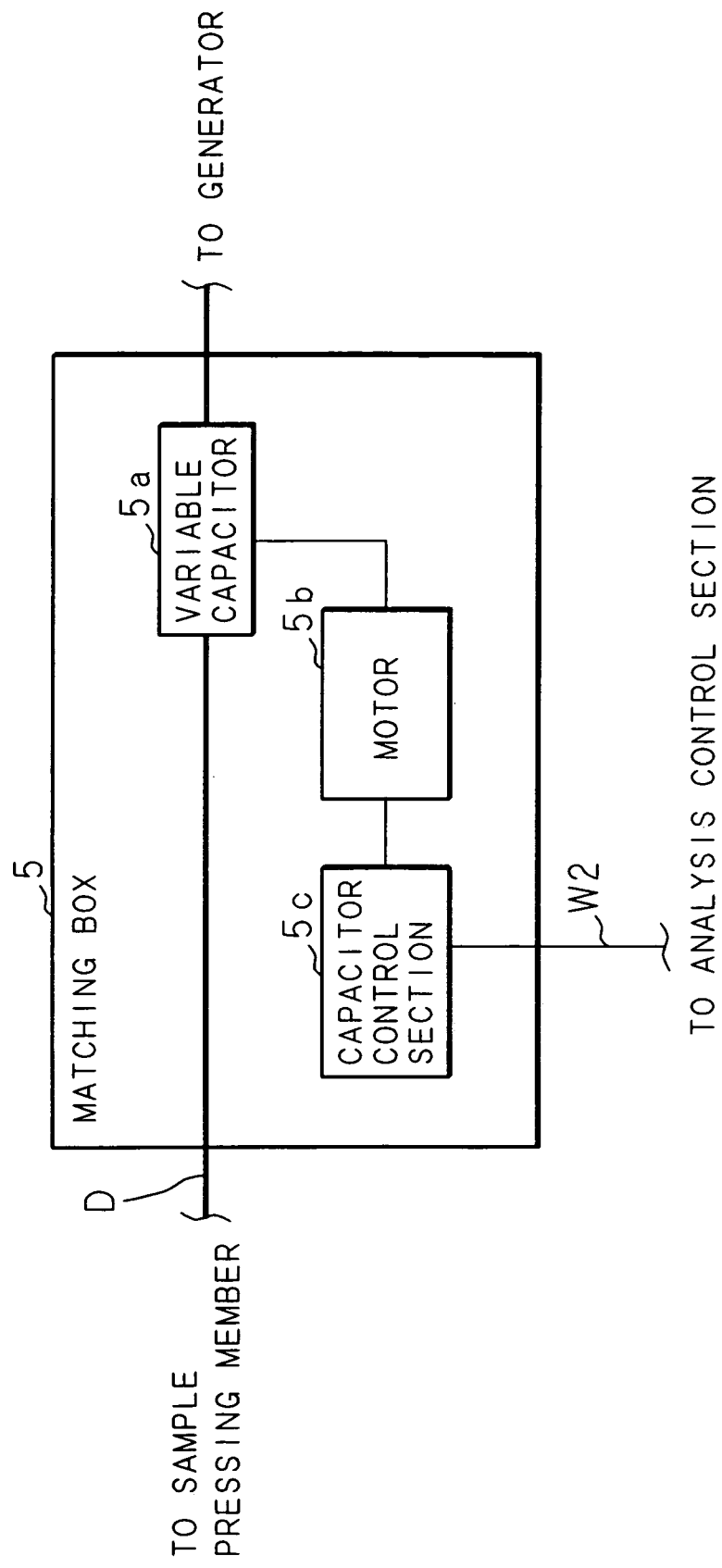
FIG. 6 is a block diagram showing an internal configuration of a matching box.

FIG. 6 is a diagram showing an internal configuration of the matching box 5 of the power supply section 3. The matching box 5 has, in the case of the continuous application mode, a variable capacitor 5a for adjusting the output mode of a high frequency voltage generated by the generator 4; a motor 5b for adjusting the electrical capacity of the variable capacitor 5a; and a capacitor control section 5c for controlling the drive of the motor 5b and the like.

The variable capacitor 5a changes its own electrical capacity according to the drive of the motor 5b and adjusts modules and phases. The capacitor control section 5c is connected to the analysis control section 8 through a second connecting cord W2, and controls the drive of the motor 5b based on a notification signal as to the setting mode which is transmitted to the matching box 5 from the analysis control section 8.

Specifically, in the case where the capacitor control section 5c receives a notification signal about the intermittent application mode, the capacitor control section 5c stops the rotation of the motor 5 and controls to fix the electrical capacity of the variable capacitor 5a to a constant value. On the other hand, in the case where the capacitor control section 5c receives a notification signal about the continuous application mode, the capacitor control section 5c controls the drive of the motor 5b and changes the electrical capacity of the variable capacitor 5a so as to make the reflection value Pr from the sample S minimum. Note that when the reflection value Pr is minimum, the capacitor control section 5c does not control to change the electrical capacity of the variable capacitor 5a.

The gas supply section 6 shown in FIG. 2 has a cylinder (not shown) in which is filled an inert gas such as an argon gas, a mixed gas of an inert gas, or the like; and a solenoid valve (not shown) which is connected to a third connecting cord W3 and opens and closes by control of a second substrate 17 of the analysis control section 8, thereby supplying an inert gas from the cylinder. The glow discharge optical emission spectrometer 1, though not shown in FIG. 2, includes a vacuuming device for creating, prior to gas supply from the gas supply section 6, a vacuum by sucking out the air inside the glow discharge tube 2.

The spectroscope 7 for measuring light L from the glow discharge tube 2 has, as shown in FIG. 2, a first slit 7a which allows the light L to be transmitted therethrough; a diffraction grating 7b for splitting the light L having been transmitted through the first slit 7a; a second slit 7c which allows the lights having been split into wavelengths corresponding to the components to be measured, to be transmitted therethrough; a plurality of photomultipliers 7d for continuously measuring the intensities of the lights having been transmitted through the second slit 7c. The photomultipliers 7d are connected to the analysis control section 8 by means of a bundle of connecting lines W4 consisting of a plurality of cords being gathered up. In the present invention, the analysis control section 8 obtains a measured value of the intensity of light through the bundle of connecting lines W4 and at a required timing.

The analysis control section 8 shown in FIG. 2 employs a computer. The analysis control section 8 has mounted therein a first substrate 16 which is connected to the bundle of connecting lines W4 extending from the photomultipliers 7d, and which obtains measured values from the spectroscope 7; and the second substrate 17 used to establish a connection to the first connecting cord W1 extending from the generator 4, the second connecting cord W2 extending from the matching box 5, and the third connecting cord W3 extending from the gas supply section 6. Each of the substrates 16 and 17 is connected via an internal bus 8a to a CPU 8b, a hard disk device 8c, and a memory 8d for temporarily storing files, data, and the like which are associated with processes. To the internal bus 8a there is connected a monitor device 8e through an external connecting line W5 and the vacuuming device which is not shown is connected to the second substrate 17.

The second substrate 17 has a circuit section designed for the intermittent application mode and a circuit section designed for the continuous application mode. As will be described later, when the contents indicating the mode which is inputted by a user (measurer) is transmitted to the second substrate 17 by control of the CPU 8b, one of the circuit sections corresponding to the transmitted mode goes into operation, and a signal instructing to perform a voltage application in the received mode is outputted to the generator 4 from the circuit section being in operation.

In the case of the intermittent application mode, the second substrate 17 controls, as a timing instruction means, to output to the generator 4 a signal instructing about an application timing for one cycle of intermittent application shown in FIG. 5 (i.e., a timing of a unit of application time T1 during an intermittent application time). This signal contains parameters such as the peak voltage value of a high frequency voltage, a reference voltage value used to make an adjustment according to an impedance value, and an application frequency and the occupied ratio of a voltage application which are set by the user. Furthermore, the second substrate 17 performs, when outputting to the generator 4 a signal instructing about an application timing, a process of simultaneously outputting, via the internal bus 8a, to the first substrate 16 a signal notifying about the application timing.

The second substrate 17 performs a process of outputting to the matching box 5 a notification signal, called a manual adaptation, which notifies about the intermittent application mode, and also performs a process of outputting, regardless of the type of the mode, instructions as to control against the gas supply section 6 and the vacuuming device.

The first substrate 16 corresponds to a measured-value obtaining means. In the case of the intermittent application mode, the first substrate 16 performs a process of obtaining a measured value from the spectroscope 7 at a timing at which the first substrate 16 receives from the second substrate 17 a signal notifying about an application timing. When this timing is viewed from the entire glow discharge optical emission spectrometer 1, the first substrate 16 is to obtain a measured value from the spectroscope 7 in synchronization with an intermittent application to the sample S, i.e., at a timing at which an application for one cycle of intermittent application is instructed. Hence, during intermittent application, the analysis control section 8 (the first substrate 16) obtains only those measured values each of which is present in each unit of application time T1 shown in FIG. 5, and does not obtain a measured value during a time period in which a voltage application is not performed. As a result, it is possible to prevent various types of noise caused during a non-application time from being introduced in the measured values, and accordingly, highly-accurate measured values can be obtained.

Figure 7:
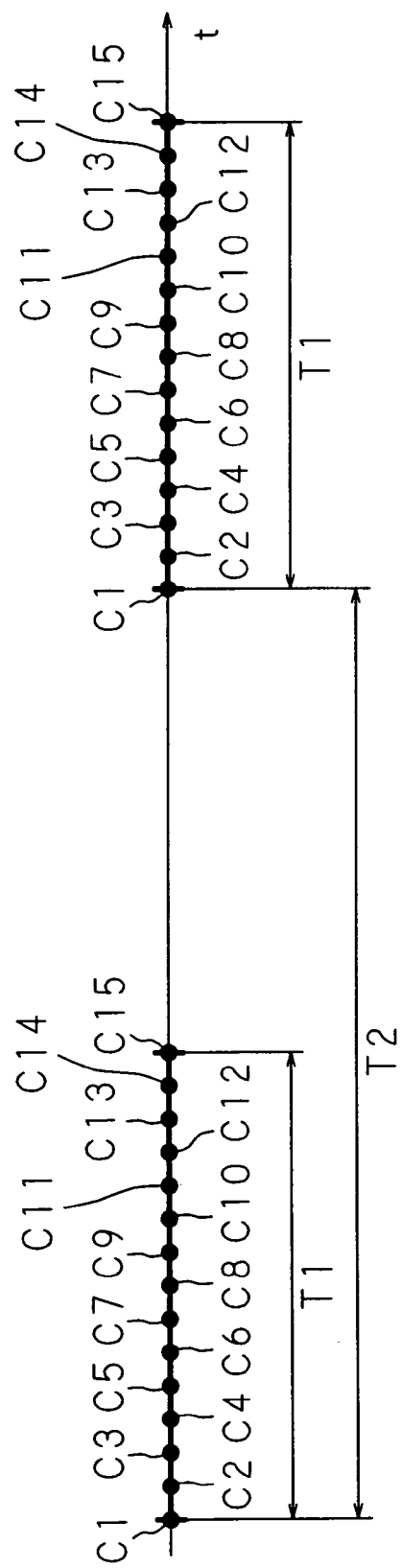
FIG. 7 is a diagram showing timings at which measured values are obtained during intermittent application.

Moreover, in the case of the intermittent application mode, the fist substrate 16 obtains, as shown in FIG. 7, a measured value the number of times (e.g., 15 times) per unit of application time T, which is notified from the CPU 8b. Specifically, at the first obtaining timing C1 a measured value is obtained at a timing conforming to the starting point timing of a unit of application time T1, and subsequently, from the second obtaining timing C2 to the fifteenth obtaining timing C15 measured values are obtained at a timing falling within the end point timing of the unit of application time T1. In the first substrate 16, the time intervals between the obtaining timings C1 to C15 are also based on an instruction from the CPU 8b. As described above, since a measured value is obtained 15 times per unit of application time T1, the glow discharge optical emission spectrometer 1 of the present invention can obtain a large number of measured values in a short period of time and complete the measurement before an adverse effect by attrition of the sample S caused by sputtering becomes noticeable.

Figure 8A:
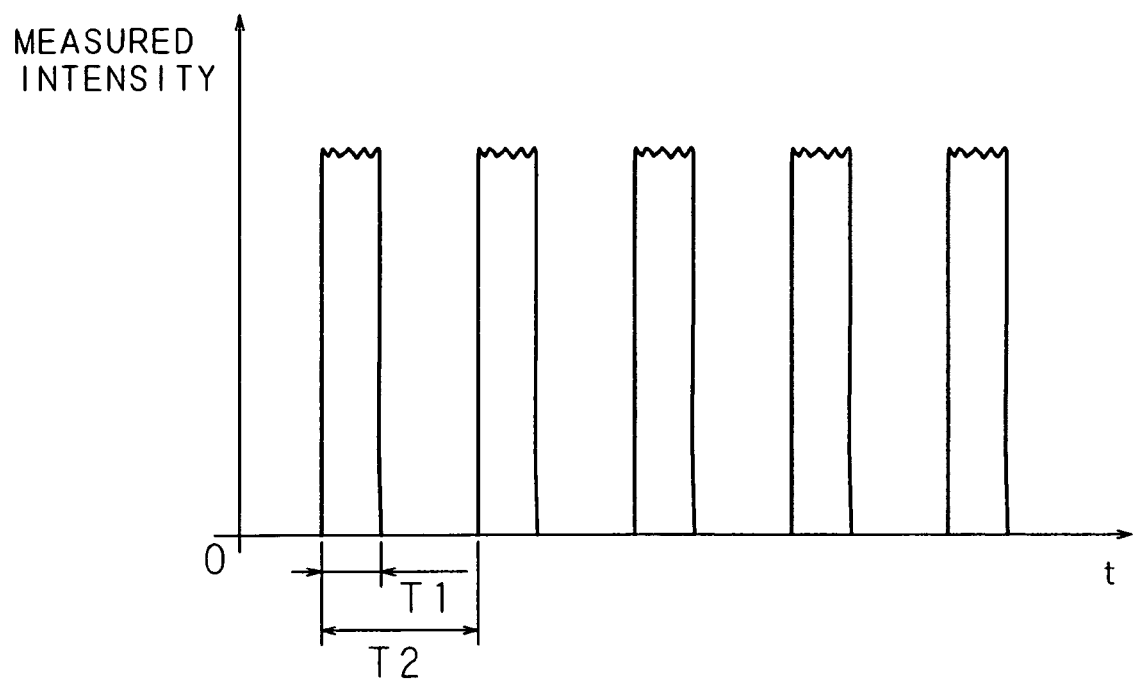
FIG. 8A is a graph showing the measured intensities of the measured values in the intermittent application mode.
Figure 8B:
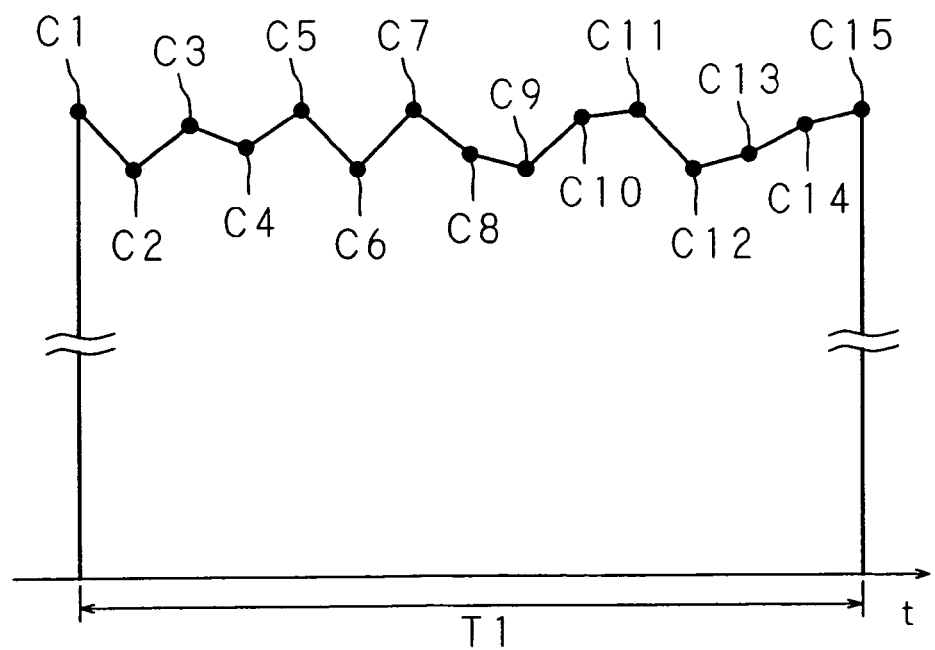
FIG. 8B is a graph showing an enlarged view of a portion corresponding to a unit of application time T1 shown in FIG. 8A.

FIG. 8A is a graph showing the measured intensities of the measured values obtained by the first substrate 16, with respect to the time axis t. As described above, the first substrate 16 performs 15 measurements per unit of application time T1, and thus, the measurement results are represented as columnar graphs each provided per unit of application time T1. FIG. 8B is a graph showing an enlarged view of a portion corresponding to one unit of application time T1 shown in FIG. 8A, and showing a line formed by connecting the values measured at 15 obtaining timings C1 to C15.

The first substrate 16 outputs the obtained measured values to the memory 8d, and the measured values are subjected to a required editing process for measurement results, based on a process performed by the CPU 8b, as will be described later.

The CPU 8b of the analysis control section 8 performs various processes based on a program stored on the hard disk device 8c. For instance, the CPU 8b receives a setting of either the intermittent application mode or the continuous application mode which is inputted by the user, and allows the first substrate 16 and a required circuit of the second substrate 17 to operate according to the set mode. In addition, the CPU 8b performs an editing process on the measured values obtained by the first substrate 16, and analyzes the concentration of the composition of the sample S, and the like.

Figure 9:
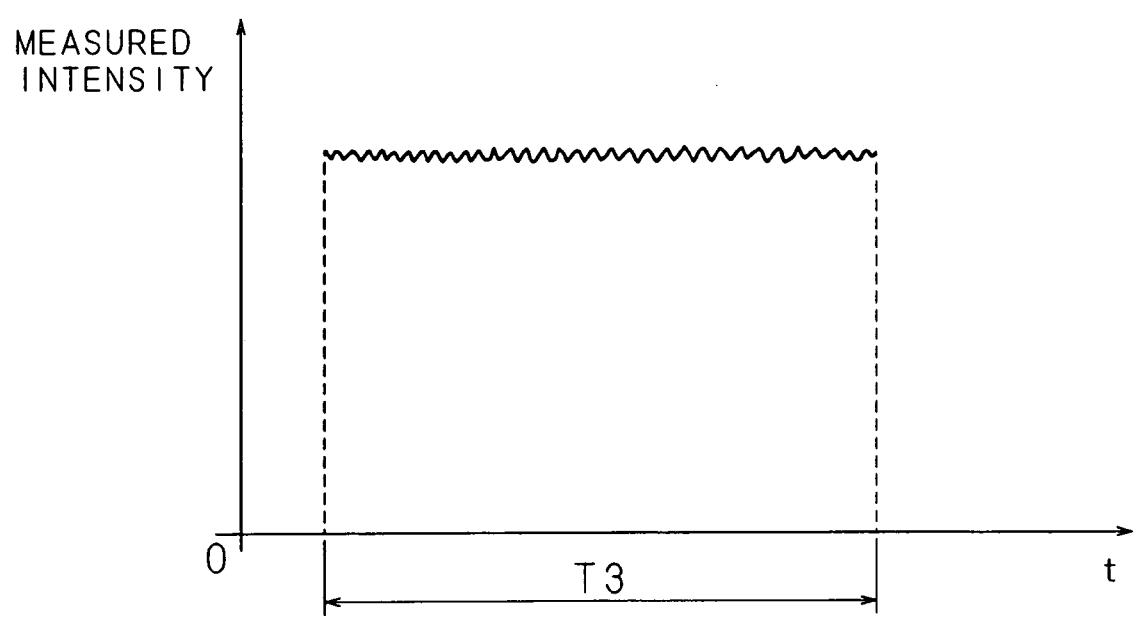
FIG. 9 is a graph in which the measured values are connected.

The editing process performed on the measured values by the CPU 8b includes extracting, from the measured values in the form shown in FIG. 8A, only those measured values each of which is present in each unit of application time T1, and connecting the extracted measured values, thereby creating data of a continuous graph in which, as shown in FIG. 9, each measured value is associated with the total time of each application time during intermittent application. In the graph shown in FIG. 9, time T3 on the time axis t is the time obtained by multiplying the measured unit of application time T1 by the number of applications. The CPU 8b outputs the data of the graph shown in FIG. 9 to the monitor device 8e so that the measurement results can be displayed on the monitor device 8e in a user-understandable form.

Furthermore, the CPU 8b can perform a process of calculating the average measured value for the total application time by adding up the measured intensities of the measured values and then dividing the added result by the time T3. In addition, the CPU 8b can calculate the average measured value for the total number of measurements by adding up the measured intensities of the measured values and then dividing the added result by the total number of measurements. The CPU 8b can allow such calculated results to be displayed on the monitor device 8e. By thus calculating various average measured values, the analysis of the sample S can be easily performed.

In addition to the processes associated with measured values, the CPU 8b allows a menu screen 20 shown in FIG. 10 to be displayed on the monitor device 8e, and performs a process of receiving various setting items. The data of the menu screen 20 itself is stored on the hard disk device 8c. The data structure allows the user to select a required content for each of the items including a mode selection, a frequency setting, an occupied ratio setting, and a setting for the number of measurements. When the menu screen 20 is displayed on the monitor device 8e, the user is allowed to perform an input operation on an item using a mouse, a keyboard, or the like (not shown in FIG. 2) which is connected to the analysis control section (computer) 8.

A numeric value selection for the items on the menu screen 20, including the frequency setting, occupied ratio setting, and setting for the number of measurements, can be made only when the intermittent application mode is selected in the mode selection. In the present embodiment, the item of the frequency setting allows the user to select, as an application frequency, a numeric value within a range of 1 Hz to 3000 Hz, the item of the occupied ratio setting allows the user to select a numeric value within a range of 0.125 to 0.9375, and the item of the setting for the number of measurements allows the user to select, as the number of measurements for a unit of application K, a numeric value within a range of 1 to 100. Note that these selection ranges are only examples and can be appropriately changed according to the specifications of the glow discharge optical emission spectrometer 1.

When an input is performed on each item on the above-described menu screen 20, the CPU 8b receives the inputted contents and performs a setting for the items, and then performs, based on the settings, a required control on the first substrate 16 and the second substrate 17 and notifies each of the substrates 16 and 17 of the set contents. Specifically, the CPU 8b notifies each of the substrates 16 and 17 of the set mode, and also notifies, in the case where the intermittent application mode is set, each of the substrates 16 and 17 of the contents of required setting items.

In addition to the above-described processes, the CPU 8b also performs a process of setting various parameters, such as a gas supply pressure of the gas supply section 6, the peak voltage value of a high frequency voltage, a reference time for analysis, and a reference voltage value, which are inputted by the user on other menu screens, and then notifying each of the substrates 16 and 17 of the settings; a process of storing the set contents on either the hard disk device 8c or the memory 8d; a process associated with analysis results; and the like.

Figure 11:
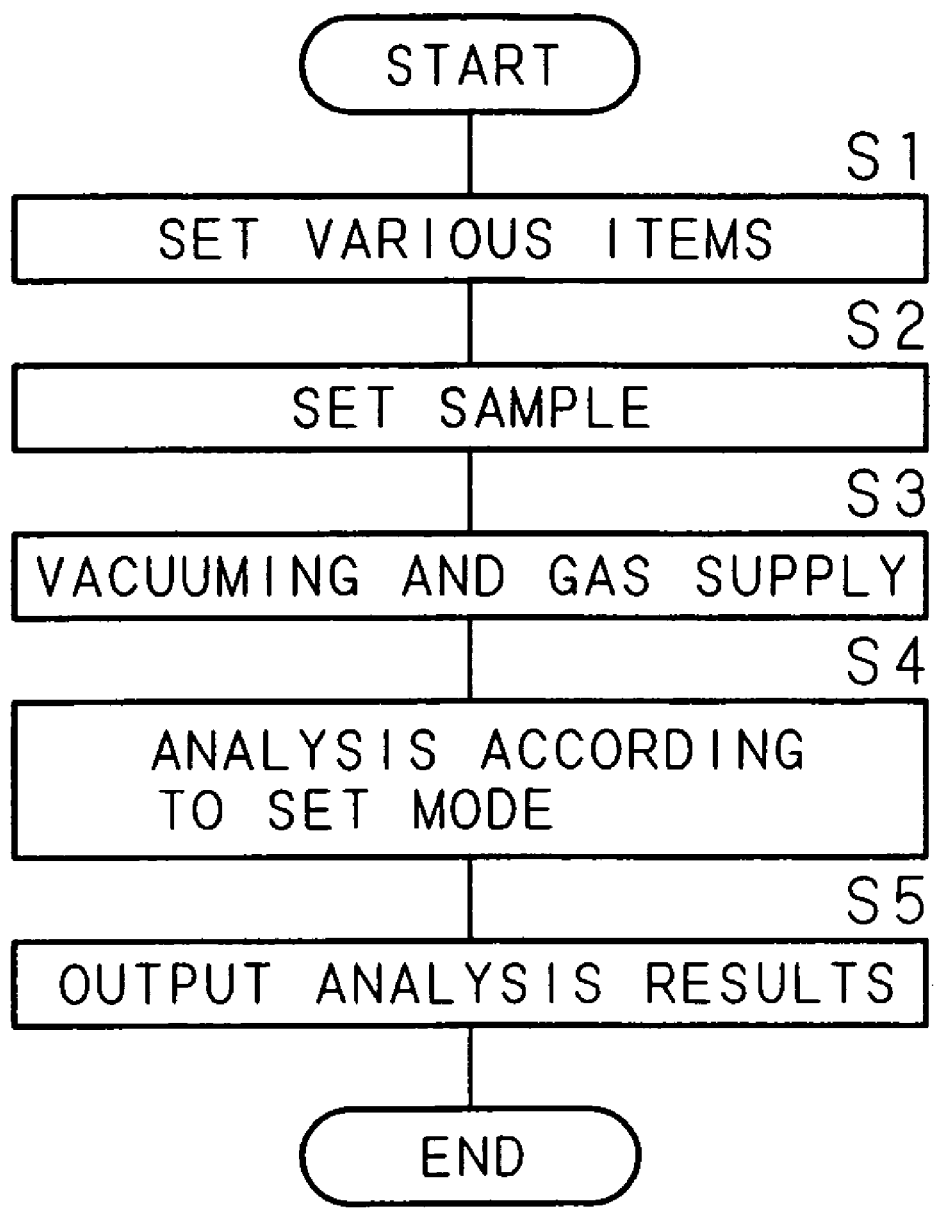
FIG. 11 is a first flowchart showing the overall processing steps for the glow discharge optical emission spectrometer.

Now, the overall processing flow for an analysis performed by the glow discharge optical emission spectrometer 1 having the above-described configuration will be described with reference to a first flowchart of FIG. 11.

First, on the menu screen 20 shown in FIG. 10, and the like, various items, such as a mode, a frequency for a voltage application, an occupied ratio, and the number of measurements, are set (S1), and then a sample S is set at the glow discharge tube 2 of the glow discharge optical emission spectrometer 1, as shown in FIGS. 2 and 3 (S2).

Thereafter, vacuuming is performed on the inside the glow discharge tube 2 using the vacuuming device, and then an inert gas (argon gas) required for measurement is supplied from the gas supply section 6 (S3). In this condition, a voltage application according to the set mode is performed, and an analysis is performed on the sample S (S4).

In the process associated with the analysis, first, argon ions formed from the argon gas supplied to the glow discharge tube 2 collide with the surface of the sample S, thereby causing sputtering, and particles containing ions pop out of the surface of the sample S. Then, at the time when the particles excited in a plasma return to the ground state, light emission which is characteristic of the elements occurs. Further, light L obtained through the light emission is split using the spectroscope 7, and the intensity of each split light is measured. Thereafter, the analysis control section 8 obtains the measured values from the spectroscope 7, and analyzes elements and the like contained in the sample S based on the obtained measured values. The analysis control section 8 outputs the results obtained through the analysis to the external device (S5), and allows the analysis results to be displayed on the monitor device 8e.

Figure 12:
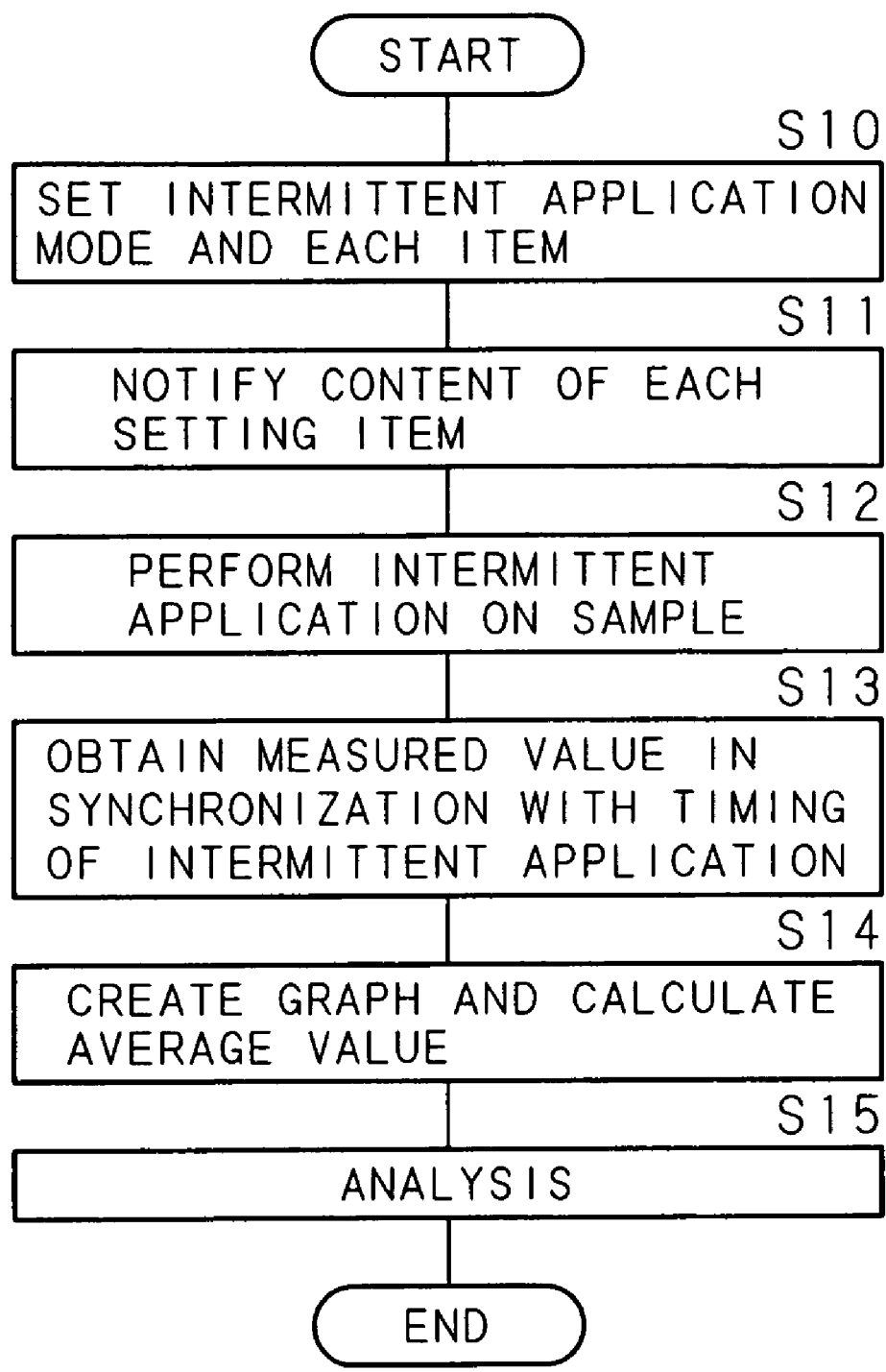
FIG. 12 is a second flowchart showing processing steps according to a glow discharge optical emission spectrometry in the intermittent application mode.

A second flowchart of FIG. 12 shows a series of contents associated with a processing method (glow discharge optical emission spectrometry) in the intermittent application mode.

First, the glow discharge optical emission spectrometer 1 sets the intermittent application mode and the content of each item which are inputted by the user (S10). Then, the CPU 8b of the analysis control section 8 notifies each of the substrates 16 and 17 of the fact that the intermittent application mode is set, and the content of each setting item (S11).

When the second substrate 17 receives a notification from the CPU 8b, the circuit section on the intermittent application mode side goes into operation, and a signal instructing to perform an intermittent application in accordance with the set contents is outputted to the generator 4. The generator 4 having received an instruction performs an intermittent application on the sample S such that, as shown in FIG. 5, the voltage is intermittently applied by alternately repeating an application and a non-application of a high frequency voltage (S12). Note that when the second substrate 17 instructs the generator 4 about the timing of an intermittent application, the second substrate 17 also notifies the first substrate 16 of the timing per unit of application.

On the other hand, when the first substrate 16 receives a notification from the CPU 8b, the first substrate 16 obtains a measured value from the spectroscope 7 in synchronization with the timing of an intermittent application which is outputted from the second substrate 17 (S13). At this time, the first substrate 16 obtains a measured value the number of times which is set for each unit of application time T1. Thereafter, the CPU 8b performs a process of creating a graph, such as the one shown in FIG. 9, and calculating an average value, based on the obtained measured values (S14). Then, the CPU 8b performs a quantitative analysis or a qualitative analysis on the samples based on the calculated results and the like (S15).

As described above, in the glow discharge optical emission spectrometer 1 of the present invention, since, in the case of the intermittent application mode, a large number of measured values are obtained in a short period of time in synchronization with an intermittent application, the adverse effect by attrition of the sample S caused by sputtering can be significantly reduced in comparison with conventional cases, and the value of a voltage applied to the sample S can be made larger in comparison with the case where a voltage application is continuously performed. Therefore, by application of a high voltage value, high-level measured values can be obtained; in addition, by obtaining a measured value in synchronization with an intermittent application, it is possible to obtain measured values in which noise components introduced during a measurement at a non-application time are removed. Consequently, the obtaining of a large number of high-level and highly-accurate measured values in a short period of time is realized.

In order to verify the specific effect of the present invention, the inventor of the present invention has carried out, for comparison, an experiment in which measured values were obtained by conventional continuous voltage application, and an experiment in which measured values were obtained in synchronization with an intermittent application according to the present invention, with the use of a sample (JIS153-13) containing 0.184% of carbon (C). As a result, in the case of obtaining measured values by conventional continuous application, the average voltage value which corresponds to the intensity for the measurement was 0.9305 V and the relative standard deviation (RSD) was 0.645%. On the other hand, in the case of obtaining measured values by intermittent application of the present invention, the average voltage value was 3.82235 V and the relative standard deviation was 0.030%, i.e., the value of the relative standard deviation is reduced by one order of magnitude compared to the conventional value. From this, it has been found out that by obtaining measured values in synchronization with an intermittent application, it becomes possible to perform an application of a high voltage value without causing problems, and the measured values to be obtained become highly accurate.

The content of the aforementioned experiment in which measured values were obtained by intermittent application of the present invention is described in detail below. The obtaining of a measured value 1000 times per second was performed for five seconds in total. For the first 1000 times the average voltage value was 3.822933 V, from 1001 to 2000 times the average voltage value was 3.823953 V, from 2001 to 3000 times the average voltage value was 3.822308 V, from 3001 to 4000 times the average voltage value was 3.821314 V, and from 4001 to 5000 times the average voltage value was 3.821231 V, and the standard deviation (SD) was 0.00114.

It should be noted that the glow discharge optical emission spectrometer 1 according to the present invention can be applied in various modifications other than the above-described embodiment. For instance, in the total 15 obtaining timings C1 to C15 of measured values shown in FIGS. 7 and 8B, a measured value may not be obtained at the first timing (e.g., the obtaining timing C1) and the last timing (e.g., the obtaining timing C15) and a measured value may be obtained only at the middle timings (e.g., the obtaining timings C2 to C14).

Specifically, even when the first substrate 16 obtains measured values in accordance with a notification from the second substrate 17, when, for example, the CPU 8b of the analysis control section 8 has a large processing burden or lots of signal transmission and reception, the timing at which a measured value is obtained may be a bit off from the actual timing at which each unit of application of intermittent application is performed on the sample S. Therefore, as described above, by not obtaining a measured value at the first and last timings, it is possible to surely prevent the obtaining of measured values in which are introduced noise components during a non-application time. The obtaining of such measured values can be realized by changing the content of control against the second substrate 17, etc., of the CPU 8b and the contents of processes for the substrates 16 and 17, etc.

The timing at which the first substrate 16 obtains a measured value may be set to conform to the time when the voltage measuring section 4c of the generator 4 shown in FIG. 4 detects a voltage application to the sample S. In this case, the voltage measuring section 4c functions as an application detection means. When the voltage measuring section 4c has detected a reflection value Pr which is reflected by voltage application to the sample S and returned, the voltage measuring section 4c performs a process of notifying the second substrate 17 of the detection via the control section 4b, and the second substrate 17 notifies the first substrate 16 of the detection. Thus, when the first substrate 16 receives from the second substrate 17 a notification that the voltage measuring section 4c has detected a voltage application to the sample S, the first substrate 16 obtains a measured value at the timing of reception of the notification. By doing so, the first substrate 16 can obtain a measured value from the spectroscope 7 at the timing at which a voltage application to the sample S is detected, whereby the degree of matching of the obtaining timing of a measured value to the actual timing of intermittent application increases, and a measurement in accordance with light emission can be performed.

Furthermore, the obtaining of measured values from the spectroscope 7 can also be done in a software manner based on a process defined by a program which is stored on the hard disk device 8c. In this case, a process is perform such that the first substrate 16 sequentially obtains values measured by the spectroscope 7 and temporarily stores the values in the memory 8d, and the CPU 8b extracts, from a series of these measured values, only those measured values each of which corresponds to each unit of application time T1 corresponding to a unit of application K shown in FIG. 5, and then obtains measurement results shown in FIG. 8A. By obtaining such measured values, it becomes unnecessary to perform the notification process between the first substrate 16 and the second substrate 17, and the processing burden, particularly, on the circuit section of the second substrate 17 can be reduced.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. A glow discharge optical emission spectrometer for measuring, with a spectroscope, an intensity of light emission from a glow discharge generated by application of an alternating voltage to a material to be analyzed, the glow discharge optical emission spectrometer comprising:
   an intermittent application section for intermittently applying an alternating voltage to the material to be analyzed; and
   a measured value obtaining section for obtaining a value measured by the spectroscope, in synchronization with an intermittent application which is performed by the intermittent application section.

2. The glow discharge optical emission spectrometer according to claim 1, wherein
   the measured value obtaining section obtains a measured value from the spectroscope a plurality of times per application during one cycle of intermittent application.

3. The glow discharge optical emission spectrometer according to claim 1, further comprising
   a number-of-times reception section for receiving a number of times to obtain a measured value per application during one cycle of intermittent application,
   wherein the measured value obtaining section obtains from the spectroscope a measured value the number of times received by the number-of-times reception section.

4. The glow discharge optical emission spectrometer according to claim 1, further comprising
   a creation section for creating continuous-graph data in which the measured values obtained by the measured value obtaining section are associated with application times during intermittent application.

5. The glow discharge optical emission spectrometer according to claim 1, further comprising
   a calculation section for calculating an average measured value of the measured values obtained by the measured value obtaining section, for an application time or a number of measurements.

6. The glow discharge optical emission spectrometer according to claim 1, further comprising
   a timing instruction section for instructing the intermittent application section about an application timing for an application of one cycle of intermittent application, wherein the measured value obtaining section obtains a measured value at the timing instructed by the timing instruction section.

7. The glow discharge optical emission spectrometer according to claim 1, further comprising an application detection section for detecting an application of an alternating voltage to the material to be analyzed, wherein the measured value obtaining section obtains a measured value at a timing at which the application detection section detects the application of an alternating voltage.

8. The glow discharge optical emission spectrometer according to claim 1, further comprising a time reception section for receiving a proportion of an application time in one cycle of intermittent application, wherein the intermittent application section performs an intermittent application based on the proportion of an application time received by the time reception section.

9. The glow discharge optical emission spectrometer according to claim 1, further comprising a number-of-times reception section for receiving a number of applications per unit time for intermittent application, wherein the intermittent application section performs an intermittent application based on the number of applications received by the number-of-times reception section.

10. A glow discharge optical emission spectrometry using a glow discharge optical emission spectrometer having a voltage application section, a spectroscope, and an analysis control section, in which a glow discharge is generated by application of an alternating voltage to a material to be analyzed by means of the voltage application section, an intensity of light emission from the glow discharge is measured with the spectroscope, and a value measured by the spectroscope is obtained by the analysis control section, the glow discharge optical emission spectrometry comprising the steps of:

intermittently applying an alternating voltage to the material to be analyzed by the voltage application section; and obtaining a value measured by the spectroscope by the analysis control section in synchronization with an intermittent application to the material to be analyzed.

* * * * *